United States Patent [19]

Brennan

[11] 4,222,392

[45] Sep. 16, 1980

[54] ALLERGY TESTING DEVICE WITH VENTED BASE

[75] Inventor: Louis G. Brennan, Stockton, Calif.

[73] Assignee: Alier-Screen, Inc., Stockton, Calif.

[21] Appl. No.: 41,957

[22] Filed: May 23, 1979

Related U.S. Application Data

[63] Continuation-in-part of Ser. No. 939,442, Sep. 5, 1978.

[51] Int. Cl.³ .............................................. A61B 10/00
[52] U.S. Cl. ...................................... 128/743; 128/253
[58] Field of Search ............... 128/743, 253; 206/364, 206/439

[56] References Cited

U.S. PATENT DOCUMENTS

| | | | |
|---|---|---|---|
| 2,522,309 | 9/1950 | Simon | 128/253 X |
| 2,841,138 | 7/1958 | Laub | 128/743 |
| 3,034,507 | 5/1962 | McConnell et al. | 128/253 |
| 3,246,647 | 4/1966 | Taylor et al. | 128/253 |
| 3,289,670 | 12/1966 | Krug et al. | 128/743 |
| 3,444,989 | 5/1969 | Hertel et al. | 128/253X |
| 3,556,080 | 1/1971 | Hein | 128/743 |
| 3,596,660 | 8/1971 | Melone | 128/253 |
| 3,688,764 | 9/1972 | Reed | 128/253 X |

*Primary Examiner*—Kyle L. Howell
*Attorney, Agent, or Firm*—L. G. Wise

[57] ABSTRACT

An improved skin test kit comprising base well means and a plurality of injection units held in recessed depressions of the base and removable therefrom is provided with vent means for permitting gas escape during insertion of the injection units. The injection units comprise a hilt portion which may be mated with the periphery of the well depression. A vent hole communicating with a portion of the depression can vent gas through the base bottom, thereby preventing excessive pressure in the well means. The injection unit includes a hollow cannula within a hollow handle with a sharp point extending into liquid test substance in its respective well. Each cannula can be loaded with a predetermined amount of liquid by capillary action and the vent means prevents overloading and provides a controlled amount of liquid to be held in the cannula elements.

13 Claims, 6 Drawing Figures

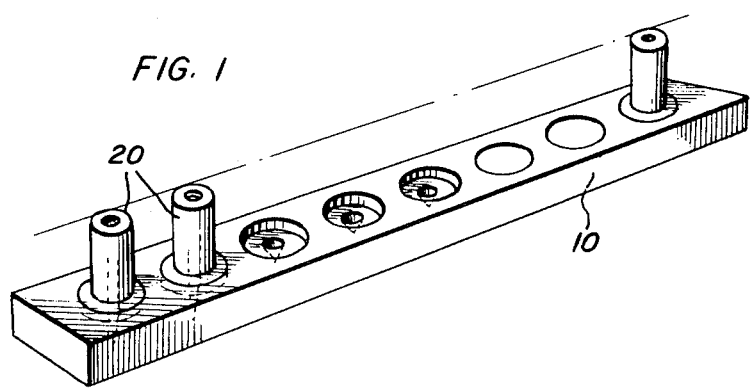
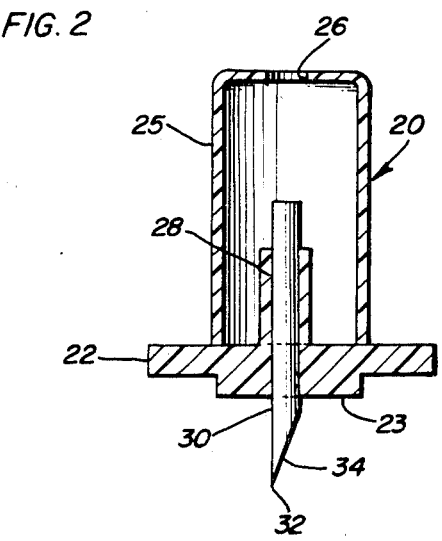

ALLERGY TESTING DEVICE WITH VENTED BASE

This application is a continuation-in-part of copending U.S. Pat. application Ser. No. 939,442, filed Sept. 5, 1978.

The present invention relates to skin testing with biological substances. In particular, it relates to medical methods and devices for allergy detection, including intracutaneous injection of biologicals, such as aeroallergens, food allergens, and other chemical substances.

Diagnosis of allergies in the past has depended upon a number of techniques for introducing various biological substances to the epidermis or dermis. In a widely-accepted testing method for inhalant allergy — the scratch test — various allergenic substances are applied by abrading or cutting the epidermal layer and contacting a liquid allergenic extract or the like with the exposed skin tissue. These test areas are often on the back of a human patient, who may be subject to many painful tests. Ths testing method is described in U.S. Pat. No, 2,841,133, which discloses a multiple unit device having a number of scarifiers in fluid communications with allergenic liquids.

The allergenic extracts may be applied manually or by automatic means. Another device for simultaneously producing multiple cutaneous sites by abrading the skin and applying biologicals is described in U.S. Pat. No. 3,289,670. The superficial scratches or abrasions produce a less severe reaction than dermal injection. If no response or weak responses are obtained in the scratch tests, less concentrated allergens may be applied to the upper extremities of the patient intradermally with a small bore needle and syringe. Reactions to these latter tests may be dramatic and even require emergency measures due to the severity of the reaction.

In another allergy testing method, a series of intradermal injections is administered by the laborious needle and syringe procedure, employing allergens in various dilutions for safety and therapeutic reasons. This serial dilution technique requries a highly skilled technician and is tedious, expensive, and often painful to the patient. However, these in vivo allergy testing methods are the primary test methods employed by allergists and otolaryngologists currently. In vitro test methods, such as radioimmunoassays, require considerable laboratory equipment and are not generally accepted for screening patients on a preliminary basis.

In addition to the airborne allergens, food allergens have been tested by skin response and are of interest to many workers in the medical field.

Besides the epidermal scratch and intradermal allergy testing methods, scarifiers have found use in applying other biological substances. For instance, vaccinations may be effected with such devices, as taught in U.S. Pat. Nos. 3,291,129 and 3,596,660. Antigens have been applied intradermally for the Heaf multiple puncture tuberculin test, as disclosed in U.S. Pat. Nos. 3,034,507 and 3,688,764.

Various attempts have been made to simplify the testing of allergies to reduce the amount of time necessary for effecting application of allergenic substances. In U.S. Pat. No. 3,556,080, multiple skin tests are administered simultaneously by applying a plurality of spaced scarifiers or puncture heads dipped in liquid antigens; however, this method has not proven entirely satisfactory due to the difficulty of locating a number of effective test sites in predetermined geometric pattern. Care must be taken in administering intradermal antigens not to inject the biological substance into a blood vessel, and this limitation on the practical use of spaced multi-point applicators has discouraged its adoption for intradermal testing.

The present invention provides a system for allergy testing wherein common antigens are incorporated in a plurality of injector units adapted for intracutaneous use. The individual injector units are intended to be supplied as part of a multiple-allergen screening and/or diagnostic kit.

A new skin test device for intracutaneous or intradermal use has been devised. This device is an applicator or injection unit having a hilt or flat plate portion and a hollow rigid handle portion attached to the plate portion on one side thereof and adapted for grasping the device. In order to pierce the skin, a hollow metal cannula scarifier element is mounted on the flat plate, extending outwardly from the flat plate opposite the handle portion a predetermined length for intradermal injection. The cannula has a sharp skin-piercing point at its lower extremity and a shaft portion extending upwardly through the flat plate into said hollow handle portion. This configuration permits the device to be loaded with a predetermined amount of fluent skin testing substance, which may be applied to the point by dipping and distributed into the hollow scarifier by capillary action.

The flat plate portion and handle portion may be integrally molded of thermoplastic resin, such as polypropylene. In the preferred embodiment of the skin test device, the handle portion comprises an elongated cylindrical tube having an open top end, and the flat plate portion has a sleeve projecting upwardly into the hollow handle portion for holding the scarifier element firmly with a predetermined prong length exposed below the hilt.

An allergy testing kit for multiple allergen screening may be assembled with a number of these applicators or injection units. A base member comprising a plurality of recessed depressions, each having a well portion adapted to receive a needle-like prong, is provided with the kit. A corresponding number of intracutaneous injection units adapted for being held in the recessed depression of the base member is provided, each comprising a hilt portion adapted for insertion into a comlementary recessed depression of the base member. A downwardly extending skin test prong portion is adapted for insertion into the corresponding well. The upwardly extending handle portion can be grasped manually for applying the injection units sequentially. In the test kit at least one ofthe prongs is loaded with a mixture of biologically active allergens, at least one of the prongs is loaded with a histamine control substance, and at least one of the prongs is loaded with a diluent devoid of biologically active substance.

The assembled kit may include a sealed package of ethylene-oxide-permeable material for containing the base member and injection units, permitting sterilization after assembly. Advantageously, the test prongs comprise a hollow cannula or hypodermic needle extending from the hilt into the base well about 0.5 to b'mm, and the handle portion is hollow to receive an upper shaft portion of the cannula. This permits capillary loading of the prongs by dipping the prong into a liquid.

The invention will be further explained in the following description and in the drawing, wherein:

FIG. 1 is a perspective view of the novel applicator system, showing the base and an injection unit;

FIG. 2 is a vertical cross-section view of an injection unit;

Figure 3:
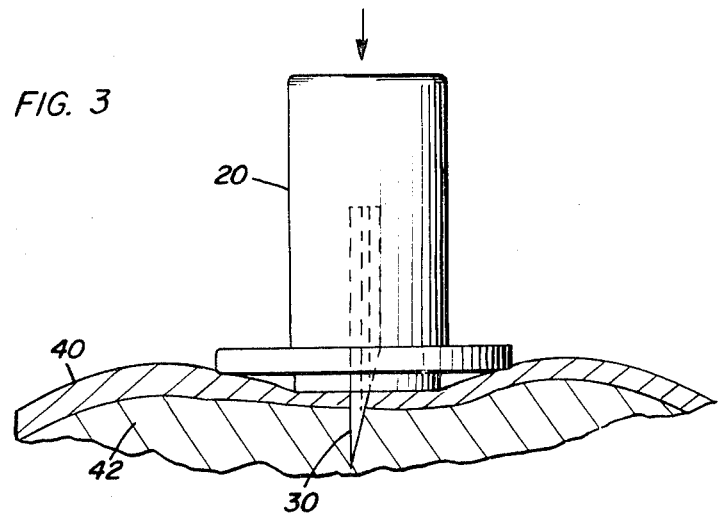
FIG. 3 is a schematic view of the injection unit during use.

In the following description, all measurements and dimensions are given in metric units and parts by weight unless otherwise stated.

Referring to FIG. 1 a base member 10 in the form of a stable flat tray is provided with a plurality of recessed depressions 12 adapted to receive individually removable applicators or injection units 20.The depressions are aligned in one or more rows for ease of identification and to facilitate use of the individual applicators. An enlarged sectional view of a single injection unit 20 is depicted in FIG. 2. In this preferred embodiment, a metal cannula is held firmly in the hilt portion 22 of the injection unit. The hilt portion comprises a flat plate, with a two-tier configuration 22, 23. The handle portion 25, shown as an elongated cylindrical tube, may have an opening at its top end or elsewhere to permit gas access to the interior of the injection unit. This aids in manufacture, liquid loading and sterilization of the fabricated applicator system. To provide a firm gripping force on the cannula 30, the flat plate or hilt portion 22 of the injection unit has a sleeve 28 projecting upwardly into the hollow handle portion. This prevents slippage during use of the cannula 30 as a scarifier, with a predetermined length exposed below the flat plate or hilt 22, 23.

During loading of liquid biologicals or other fluid materials, the cannula may be dipped into the fluid, with the skin-piercing point 32 being received into a well to prevent damaging the point. A hollow portion 34 provides a liquid reservoir on the cannula scarifier element 30, 32.

Figure 4:
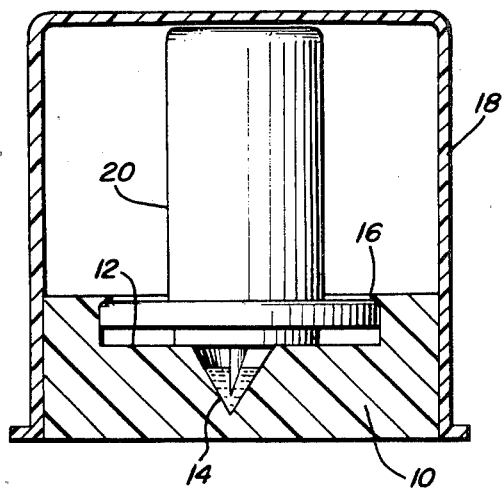
FIG. 4 is a vertical cross-section view of thepackage base containing an injection unit.

During use for skin testing, the injection unit 20 is removed manually from the base and inserted into the skin, as shown in FIG. 3. The hollow metal scarifier element 30 pierces the epidermal layer 40 and extends therethrough into the dermis 42, where the substance carried on the scarifier prong is deposited intracutaneously. Ordinarily, the injection unit is withdrawn immediately after injecting the test substance. The base member 10 may be packaged as part of a testing kit, as shown in FIG. 4. The base is provided with a plurality of circular depressions 12 into which the hilt portion of injection unit 20 is inserted. The bottom of this recessed portion is tapered downwardly to a depth of about 3mm, permitting the lower prong tip 32 to be accommodated within a well 14, which may be conoidal in shape. Prior to inserting the injection unit, a measured quantity of the particular biological substance or diluent is placed in the bottom of the well 14. In order to protect the testing kit after manufacture and sterilization, a lid 18 is placed over the base member 10, preventing the individual injection units from becoming loose. As an extra precaution, a projecting segment 16 can be molded onto the base 10 to engage or retain the hilt portion in its nested position, thus preventing dislocation of the applicator parts during shipment. The lid may be taper-fitted with the sides of base member 10 to prevent contamination of the applicator and/or antigens. The lid and base may be spot-fused to prevent disassembly prior to use. The enclosure formed by the base and lid may be pre-sterilized or, advantageously, made of a material permeable to a sterilant gas. For instance, various polyalkenes, such as polyethylene, may be employed as the package material when using ethylene oxide/freon gas for post-assembly sterilization. Alternatively, the entire testing kit may be inserted in an envelope having a gas-permeable window.

The applicator prong or skin-piercing portion of the injection unit may be made from several materials, preferably metal and hard plastics. Polished surgical steel cannulae are the prong members found to be advantageous from the standpoint of quality and reproducibility. The standard hypodermic needle or cannula of polished steel, having a bevel angle of 12.5°, provides a sharp point which can easily be inserted to the desired skin depth. A standard cannula of 15 to 25 gauge can be employed, depending upon the desired carrying capacity of the base structure and prong size. For a wide variety of biological substances, a standard 20 gauge cannula can provide the dual functions of the prong member. The diluent or fluid carrier of the biologicals is often a hydrophilic compound or mixture of chemicals which possesses a high surface tension with respect to the prong. A capillary-forming structure permits relatively large amounts of the liquid biological substances and carriers to adhere to the prong. Typically, a 20 gauge steel needle has been found to retain about 1.8 milligrams of antigen-diluent mixture after dipping.

While the amount of fluid varies according to the particular test composition and prong type, amounts from a few tenths of a milliliter to a few microliters may be feasible. For allergenic extracts of the kinds described herein, a loading of about 0.001 to 0.1 ml is preferred. Liquid pickup from the polypropylene type base would ordinarily be in the desired range if a fractional milliliter of liquid extract or chemical mixture is contained in the well. It is understood that a controlled amount of solid or semi-dried biological can be obtained by employing more or less diluent to adjust the active component of the mixture. A relatively large amount of antigen can be picked up by surface phenomena when less diluent is present. For purposes of product uniformity, the amounts of antigen components can be as set forth herein or some other standard may be established for manufacturing convenience or medical purpose.

Plastic molding compositions, such as nylons, polyalkenes, polycarbonates, acrylics, etc. can be employed in making the injection units, bases, covers, etc. Provided an effective point can be cast or molded from plastics, the entire system may be fabricated from one or more synthetic resins. In the preferred embodiments, metal prongs and thermoplastic resin, such as polypropylene or polystyrene.

The flat base of the applicator may be two-tiered with a central smaller portion adjacent the cannula and a larger portion near the handle. This type of base disguises the needle puncture and serves as a stop to control depth of penetration of the point of the test prong.

This feature makes the needle puncture virtually painless and insures repetitive, standardized penetration of the skin to the desired depth. An alternative design is a completely flat hilt.

Aside from the obvious advantage of the hypodermic needle point; i.e., sharp, relatively atraumatic skin puncture, there are other advantages. These advantages are the utilization of the inner bore of the needle, in the area of the cutting point or bevel, as an inherent capillary trough or liquid reservoir for antigen application.

The needle point may project from the circular base anywhere from 0.5 to 3.0mm or more, with 2.25mm being optimum for most applicators. The injection unit permits the length of needle point projection to be varied without changing the cavity mold used in manufacture.

The preferred injection unit of FIG. 2 is made of a molded polypropylene plastic. The cylindrical handle is hollow with a wall about 1.6mm thick. The elongated tubular shape (about 17.5 ×9.5mm diameter) permits easy grasping. The two-tier circular hilt is about 2mm thick at the inner circle (8.25 mm) and about 1.5 mm thick for the outer (15.25mm). The cannula point and shaft pierce the center of the base, which is molded with a diameter slightly less than the cannula to provide means for holding the cannula in a fixed position by radial gripping force. The cannula shaft is additionally supported by a sleeve or cylindrical upward extension of the base for a distance of about 6mm into the hollow core handle. The top of the handle is open to allow insertion of the cannula therethrough and to retain the capillary action.

Figure 5:
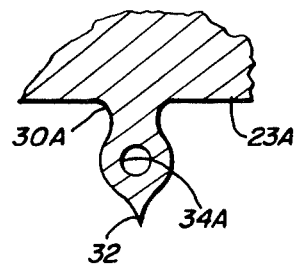
FIG. 5 is a partial cross-section view of an alternative embodiment.

An all-plastic alternative embodiment is shown in FIG. 5, an enlarged cross-sectional view showing the flat plate or hilt portion 23A having a hard prong portion 30A extending downwardly therefrom. The prong comprises a skin-piercing point 32A and a reservoir-forming open portion 34A, which is shown as an eyelet having an open area to receive liquid and hold it prior to application. The prong portion may have an overall length of 2-4mm. If sufficient liquid holding capacity is achieved by the prong configuration, the eyelet may be omitted.

While the preferred testing method employing the new applicators involves a manual sequence in which the individual injections are spaced, at least about 2 cm apart on the skin, it is understood that the invention may be adapted or modified to permit simultaneous pickup and application of the entire multi-unit assembly. This can be accomplished by a suitable manipulator device adapted to receive and hold the handle portion of the individual injection units in spaced relationship. However, the aforementioned difficulties in avoiding blood vessels must be taken into account for any such multipoint application.

Figure 6:
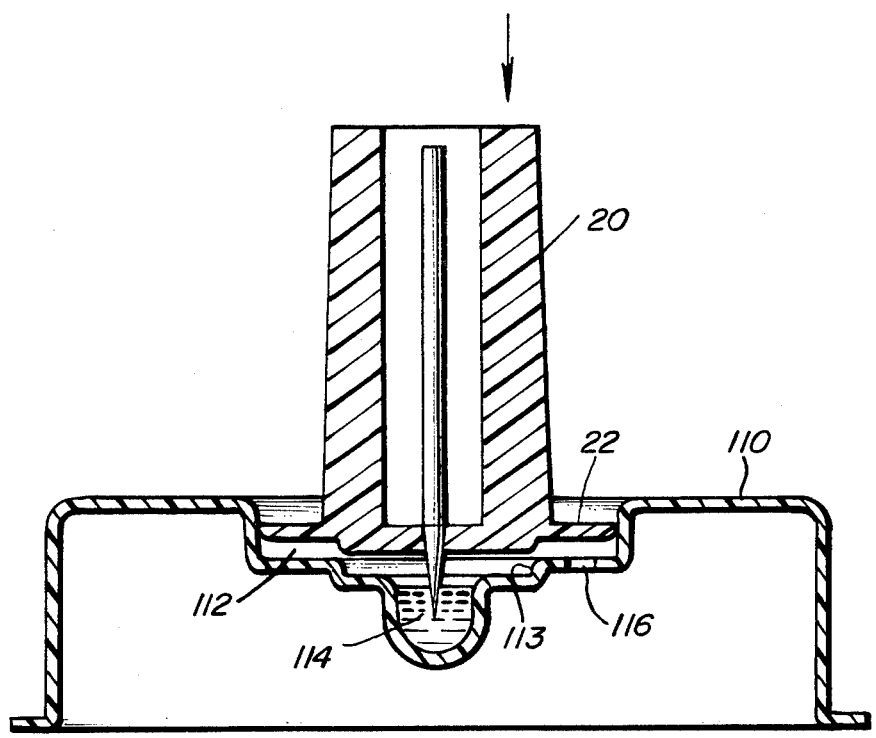
FIG. 6 is a cross-section view of a preferred embodiment of the invention, showing a modified base portion with vent means.

Another embodiment of the base is depicted in FIG. 6, which shows a vertical cross section of a molded receptacle 110 adapted to receive a standard antigen applicator 20. The circular applicator disc portion 22 for this configuration is closely mated to the periphery of the base receptacle, thereby forming a seal and resiliently holding the applicator or injection unit with sufficient firmness to prevent separation during handling.

The base portion shown comprises a concentric depression 112, annular ridge 113 and central well 114. A measured quantity of liquid antigen is placed into the center well and the injection unit is inserted into the depression with the cannula point extending into the well. A small vent hole 116 located between the annular ridge 113 and the periphery of the depression 112 permits air or other gas to be evacuated as the injection unit 20 is urged into the depression 112. By venting the trapped gas, no excessive pressure is permitted to build in the well 114, which might force an uncontrolled amount of antigen upwardly through the cannula. The hilt portion 22 of the applicator is seated against the annular ridge 113, forming an effective liquid seal.

This configuration retains a normal capillary loading of the desired amount of antigen at the lower extremity of the cannula. Pressure equalization avoids forcing excess liquid up the cannula during assembly and facilitates quality control of the device. Antigen amounts beyond the normal capillary filling might result in lack of standardization for the intracutaneous deposit.

The annuar ridge 113 may be in the form of a concentric circle or the like; however, any desired shape may be employed. The raised surface of this annulus should be sufficiently uniform to provide for liquid containment, when acting in conjunction with the opposed lower hilt surface of the applicator. It is understood that various interlocking surfaces may be employed to effect this sealing function. During assembly, excess liquid that spills outwardly form the well through the sealed annulus may be retained in the outer chamber of the base depression.

While the vent hole 116 is shown in a preferred embodiment passing through the base depression outside the annular ridge 113, the chamber may be vented through a hole in the hilt portion 22 of the injection unit or in the base area between the well 114 and annular ridge 113. In the embodiment of FIG. 6, the base may be molded of impact polystyrene advantageously, and the lid may be of the same or different material.

What is claimed is:
1. An improved allergy testing kit for allergen screening comprising:
   a base member comprising a plurality of recessed depressions each having a well portion adapted to receive a needle-like prong, each of said depressions having annular ridge means disposed within said depression surrounding said well portion;
   a plurality of intracutaneous injection units held in the recessed depressions of said base member and individually removable therefrom, each of said injection units comprising a hilt portion adapted for insertion into the recessed depression of said base member, an upwardly extending handle portion and a downwardly extending skin test prong portion adapted for insertion into a corresponding well, wherein each prong comprises a hollow metal cannula extending from the hilt into the corresponding well, and wherein the handle portion of each injection unit is hollow to receive an upper portion of said cannula, thereby permitting capillary loading of the prongs by dipping the prong into a liquid;
   at least one of said prongs being loaded with biologically active allergen; at least one of said prongs being loaded with a histamine control substance; at least one of said prongs being loaded with a diluent devoid of biologically active substance; and
   vent means for permitting gas escape during insertion of said injection units into said depressions.
2. The testing kit of claim 1 wherein said vent means comprises at least one hole communicating with that portion of said depression outside said annular ridge means for venting gas through a bottom portion of said base.
3. The testing kit of claim 1 wherein said hilt portions and said recessed depressions are closely mated, thereby forming a seal and resiliently holding said injection units.

4. The testing kit of claim wherein said hilt portion comprises a two-tier configuration with a small central tier portion adjacent said cannula and a large tier portion adjacent said handle portion.

5. The testing kit of claim 1 wherein said allergen is provided in a concentration of about 50 to 100 grams per liter.

6. The testing kit of claim 1 wherein at least one biologically active allergen substance comprises a mixture of allergens.

7. In a skin test kit for in vivo intracutaneous use including a base member having a plurality of base well means for holding liquid test substances and having depressions for receiving and holding a corresponding plurality of injection units in cooperation with lid means, each of said injection units comprising a plate portion closely mated with a peripheral area of said base well means for sealing the liquid test substances, a hollow open-top handle portion attached to the plate portion on one side thereof and adapted for manually grasping the device, and a hollow cannula element mounted on said plate and extending outwardly from said plate opposite said handle portion a predetermined length for intracutaenous injection, said cannula having a sharp skin-piercing point at its lower extremity and an upper shaft portion extending upwardly through said plate into said hollow handle portion; whereby said device may be loaded with a predetermined amount of fluent skin testing substance applied to said point by dipping and distributed into the cannula by capillary action; the improvement which comprises fluid control means comprising at least one hole communicating with said base will means forequalizing pressure in said well means and providing a controlled amount of liquid test substance to be held in the hollow cannula element of said injection units.

8. The skin test kit of claim 7 wherein said plate portion includes a two-tier configuration having a small central hilt portion adjacent said cannula and larger outer plate portion recessed from said inner hilt portion, thereby disguising puncture of said cannula into and providing standardized skin penetration.

9. The skin test kit of claim 7 comprising at least one injection unit loaded with an effective amount of admixed allergens selected from tree allergens, mold allergens, grass allergens, ragweed allergens, epidermals, dust and weed allergens; and further comprising histamine control substance and diluent control substance.

10. The skin test kit of claim 7 which comprises annular ridge means disposed within said depression and wherein said pressure equalization means comprises at least one vent hole in said base means between said ridge means and the periphery of said depression.

11. The skin test kit of claim 7 wherein said fluid control means comprises a hole in said plate portion of said injection unit.

12. The skin test kit of claim 12 wherein said plate portion and said depression are closely mated, thereby forming a seal and resiliently holding said injection unit.

13. The testing kit of claim 1 wherein said well portion and annular ridge means are substantially circular and concentric with a circular periphery of said depression, and wherein said vent means comprises a vent hole in said base between said ridge means and said periphery.

* * * * *

UNITED STATES PATENT AND TRADEMARK OFFICE
CERTIFICATE OF CORRECTION

PATENT NO. : 4,222,392
DATED : Sep. 16, 1980
INVENTOR(S) : Louis G. Brennan

It is certified that error appears in the above—identified patent and that said Letters Patent is hereby corrected as shown below:

Title Page, line [73] Assignee: Aller-Screen, Inc.

Col. 1, line 22, change "Ths" to -- This --.

Claim 7, line 33, change "forequalizing" to -- for equalizing --.

Signed and Sealed this

Fourteenth Day of April 1981

[SEAL]

Attest:

RENE D. TEGTMEYER

*Attesting Officer*    *Acting Commissioner of Patents and Trademarks*